United States Patent [19]
Griffoul et al.

[11] Patent Number: 5,447,677
[45] Date of Patent: Sep. 5, 1995

[54] APPARATUS AND METHOD FOR MAKING ABSORBENT PRODUCTS CONTAINING A FIRST MATERIAL DISPERSED WITHIN A SECOND MATERIAL

[75] Inventors: Thomas Griffoul, Jamesburg; Martin Wislinski, Edison, both of N.J.

[73] Assignee: McNeil-PPC, Inc., Milltown, N.J.

[21] Appl. No.: 71,632

[22] Filed: Jun. 2, 1993

[51] Int. Cl.⁶ ............................................. B27N 3/00
[52] U.S. Cl. ................................. 264/510; 264/517; 264/518; 264/113; 425/80.1; 425/81.1
[58] Field of Search .................. 264/37, 517, 518, 510, 264/113, 121; 425/80.1, 81.1, 82.1

[56] References Cited

U.S. PATENT DOCUMENTS

| | | | |
|---|---|---|---|
| 2,969,104 | 1/1961 | Schubert et al. | 154/1 |
| 3,768,118 | 10/1973 | Ruffo et al. | 19/156.3 |
| 3,772,739 | 11/1973 | Lovgren | 19/156.3 |
| 3,895,089 | 7/1975 | Goyal | 264/89 |
| 3,943,605 | 3/1976 | Nystrand | 19/145 |
| 3,963,392 | 6/1976 | Goyal | 425/83 |
| 4,429,001 | 1/1984 | Kolpin et al. | 428/283 |
| 4,540,454 | 9/1985 | Pieniak et al. | 156/62.2 |
| 4,592,708 | 6/1986 | Feist et al. | 425/80.1 |
| 4,598,441 | 7/1986 | Stemmler | 19/145 |
| 4,650,479 | 3/1987 | Insley | 604/358 |
| 4,652,487 | 3/1987 | Morman | 428/138 |
| 4,655,757 | 4/1987 | McFarland et al. | 604/366 |
| 4,657,802 | 4/1987 | Morman | 428/152 |
| 4,674,966 | 6/1987 | Johnson et al. | 425/82.1 |
| 4,706,338 | 11/1987 | Anspach | 19/105 |
| 4,755,178 | 7/1988 | Insley et al. | 604/367 |
| 4,904,440 | 2/1990 | Angstadt | 264/517 |
| 4,927,582 | 5/1990 | Bryson | 264/113 |
| 4,927,685 | 5/1990 | Marshall et al. | 428/74 |
| 4,931,357 | 6/1990 | Marshall et al. | 428/284 |
| 5,017,324 | 5/1991 | Kaiser et al. | 264/510 |
| 5,019,063 | 5/1991 | Marsan et al. | 604/368 |
| 5,143,680 | 9/1992 | Molnar et al. | 264/511 |
| 5,227,107 | 7/1993 | Dickenson et al. | 264/113 |

FOREIGN PATENT DOCUMENTS

| | | |
|---|---|---|
| 0151033A2 | 7/1985 | European Pat. Off. |
| 0533982A1 | 3/1993 | European Pat. Off. |

*Primary Examiner*—Mary Lynn Theisen

[57] ABSTRACT

An apparatus and method for making absorbent products in which a first material, such as absorbent fluff formed from wood pulp, is introduced into a vacuum forming chamber. A portion of the fluff is deposited into the cavity of a mold transported through the forming chamber by a forming wheel so as to form a layer of pure fluff within the bottom of the mold cavity. A second material, such as superabsorbent particles or heat stabilized fibers, is introduced into the forming chamber so that streams of the first and second materials collide within a mixing zone. As the mold continues it travel through the forming chamber, a mixture of first and second materials from the mixing zone is deposited within the mold cavity, thereby filling it. The portion of the mixture that extends above the surface of the mold is scraped off by a scarfing brush that directs the mixture back into the mixing zone, thereby creating turbulence that ensures thorough mixing of the two materials. The result is an absorbent product having a first layer formed by pure first material and a second layer formed by a mixture of the first and second materials.

35 Claims, 3 Drawing Sheets

APPARATUS AND METHOD FOR MAKING ABSORBENT PRODUCTS CONTAINING A FIRST MATERIAL DISPERSED WITHIN A SECOND MATERIAL

FIELD OF THE INVENTION

The current invention is directed to an apparatus and method for making absorbent products, such as sanitary napkins and the like, containing a first material dispersed throughout at least a portion of a second material. More specifically, the current invention is directed to the manufacture of an absorbent product having two zones—one containing pure fluff and the other containing a fluff dispersed particulate, such as superabsorbent particles.

BACKGROUND OF THE INVENTION

Traditionally, absorbent products, such as sanitary napkins, diapers, incontinence pads and the like, contained an absorbent core comprised of a soft, fluffy material, such as comminuted wood pulp. Recently, attempts have been made to incorporate various secondary material into the absorbent fluff, such as superabsorbent particles, heat stabilizing fibers, or odor absorbent material.

Unfortunately, the methods used heretofore to produce an absorbent fluff core containing such a secondary material have not been entirely suitable. Typically, a first layer of absorbent fluff is formed and a layer of the secondary material is sprinkled on top of the fluff. A second layer of absorbent fluff is then placed on top of the secondary material to complete the core. As a result, this method produces a product in which the secondary material is concentrated in fairly discrete zone within the core. In the case of superabsorbents, this concentration results is a tendency toward "gel block," whereby the swelling of the superabsorbent particles inhibits the distribution of fluid throughout the core. In the case of heat activated fibers, the concentration of heat activated fibers in a discrete layer creates an uncomfortably stiff product.

Consequently, it would be desirable to provide an apparatus and method for making absorbent products comprised of first and second materials in which the second material (i.e., superabsorbent particles) was well distributed throughout the first material (i.e., absorbent fluff). It would also be desirable to provide an apparatus and method for making absorbent products comprised of first and second layers in which the first layer contained pure first material and the second layer contained a mixture of the first and second materials.

SUMMARY OF THE INVENTION

It is an object of the current invention to provide an apparatus and method for making absorbent products comprised of first and second materials in which the second material (i.e., superabsorbent particles) was well distributed throughout the first material (i.e., absorbent fluff). This and other objects is accomplished in an apparatus for making absorbent products containing a first material and a second material dispersed throughout at least a portion of the first material, comprising (i) a chamber forming a mixing zone therein for mixing the first and second materials, (ii) means for introducing the first and second materials into the chamber, (iii) inducing means for inducing at least a portion of the first and second materials introduced into the chamber to be deposited onto a surface disposed within the chamber, and (iv) first removing means for removing from the surface at least a portion of the first and second materials deposited thereon and for directing the materials removed into the mixing zone for mixing of the first and second materials.

The current invention also includes a method for making absorbent products containing a first material and a second material dispersed throughout at least a portion of the first material, comprising the steps of (i) introducing first and second streams of first and second materials, respectively, into a chamber, (ii) depositing at least a portion of the first and second materials introduced into the chamber onto a surface within the chamber, (iii) removing at least a portion of each of the first and second materials deposited onto the surface and directing the portion in a stream into mixing contact with the second stream, thereby forming a mixture in which the second material is dispersed throughout the first material, and (iv) shaping the mixture into an absorbent product.

DESCRIPTION OF THE PREFERRED EMBODIMENT

Figure 1:
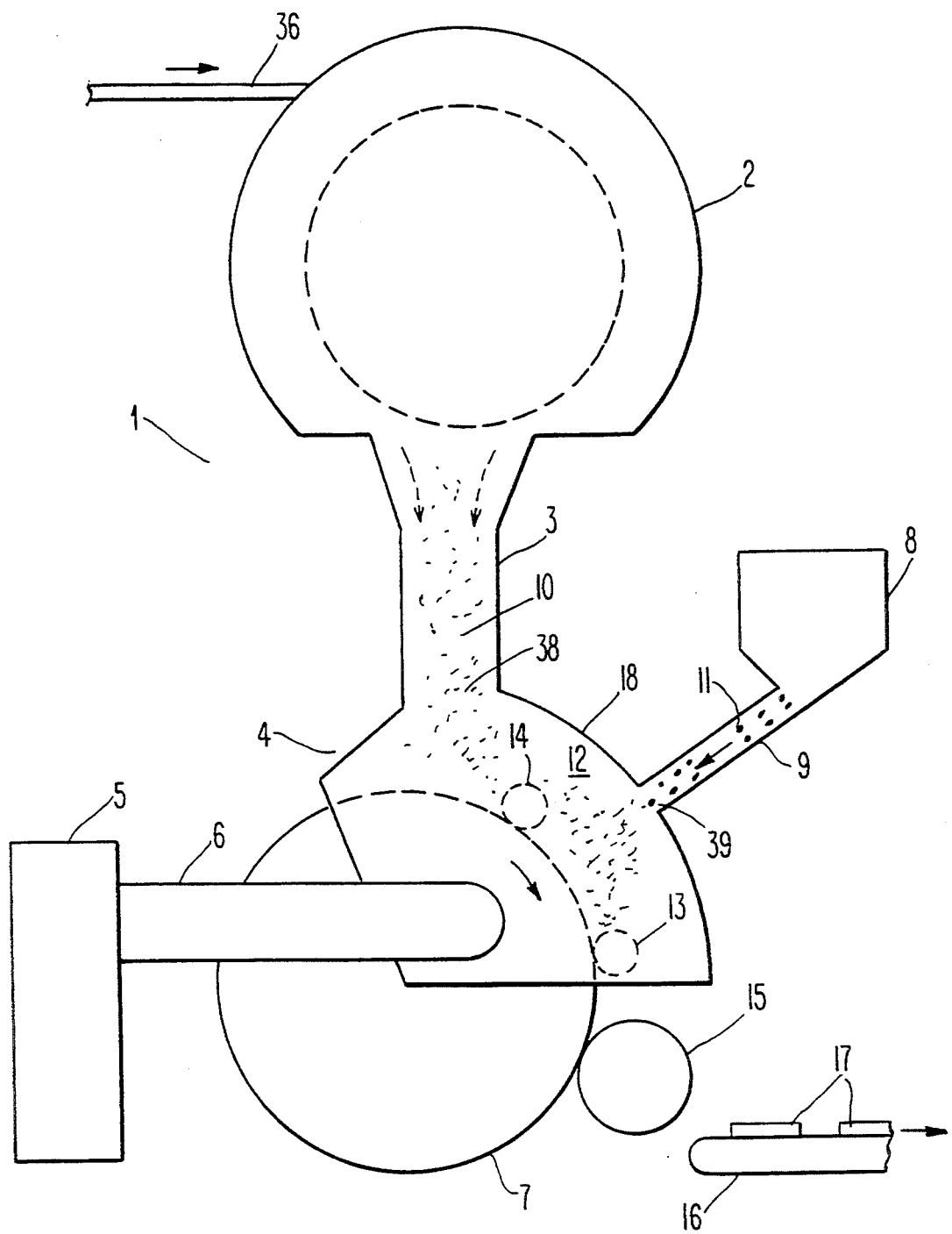
FIG. 1 is an elevation, partially schematic, of the apparatus for making absorbent products according to the current invention.

An apparatus 1 for making absorbent products according to the current invention is shown in FIG. 1. The apparatus comprises a device to de-fiberize pulp, such as a hammermill 2, and a vacuum forming unit 4 that has been modified in accordance with the teachings of the current invention. Hammermills and vacuum forming units of the type shown in FIG. 1 are described in detail in U.S. Pat. No. 4,674,966 (Johnson et al.) (assigned on its face to Winkler & Dunnebrier), U.S. Pat. No. 4,592,708 (Feist et al.) (assigned on its face to Procter & Gamble), and EPO published application No. 0,151,033 (Peterson et al.) (assigned on its face to Procter & Gamble), each of which is hereby incorporated by reference in their entirety.

As shown in FIG. 1, a web of compressed fibers of an absorbent material 36, such as wood pulp, is fed into the hammermill 2. As is conventional, in the hammermill 2, the compressed fibrous material 36 is broken down into individual fibers, collectively referred to as "fluff" 10. The fluff 10 is directed via duct 3 into the vacuum forming unit 4 drawn by the suction created within the vacuum forming unit 4 by virtue of its holding a vacuum.

The vacuum forming unit 4 is comprised of a vacuum forming chamber 12 and a forming wheel 7. The vacuum forming chamber 12 is formed within a housing 18 that is sealed to prevent loss of vacuum, as in conventional. The vacuum forming chamber housing 18 has an inlet 38 that is in flow communication with the duct 3 from the hammermill 2 so as to receive the fluff 10 and direct it in streams 25, shown in FIG. 3, into the vacuum forming chamber 12. A suitable vacuum forming chamber containing the features discussed above is disclosed in the aforementioned U.S. Pat. No. 4,592,708 (Feist et al.).

According to the current invention, the vacuum forming chamber housing 18 also has an inlet 39 that is connected via a duct 9 to a hopper 8 that contains a second material to be interspersed into the fluff 10. In the preferred embodiment, the second material comprises superabsorbent particles 11. Suitable superabsorbent particles are described in U.S. Pat. No. 4,540,454 (Pieniak et al.) (assigned on its face to Personal Products Company), which is hereby incorporated by reference in its entirety. However, the current invention could also be practiced using heat activated fibers or baking soda as the second material. Suitable heat activated fibers may be obtained from Hercules Corporation as PULPEX TM.

Figure 3:
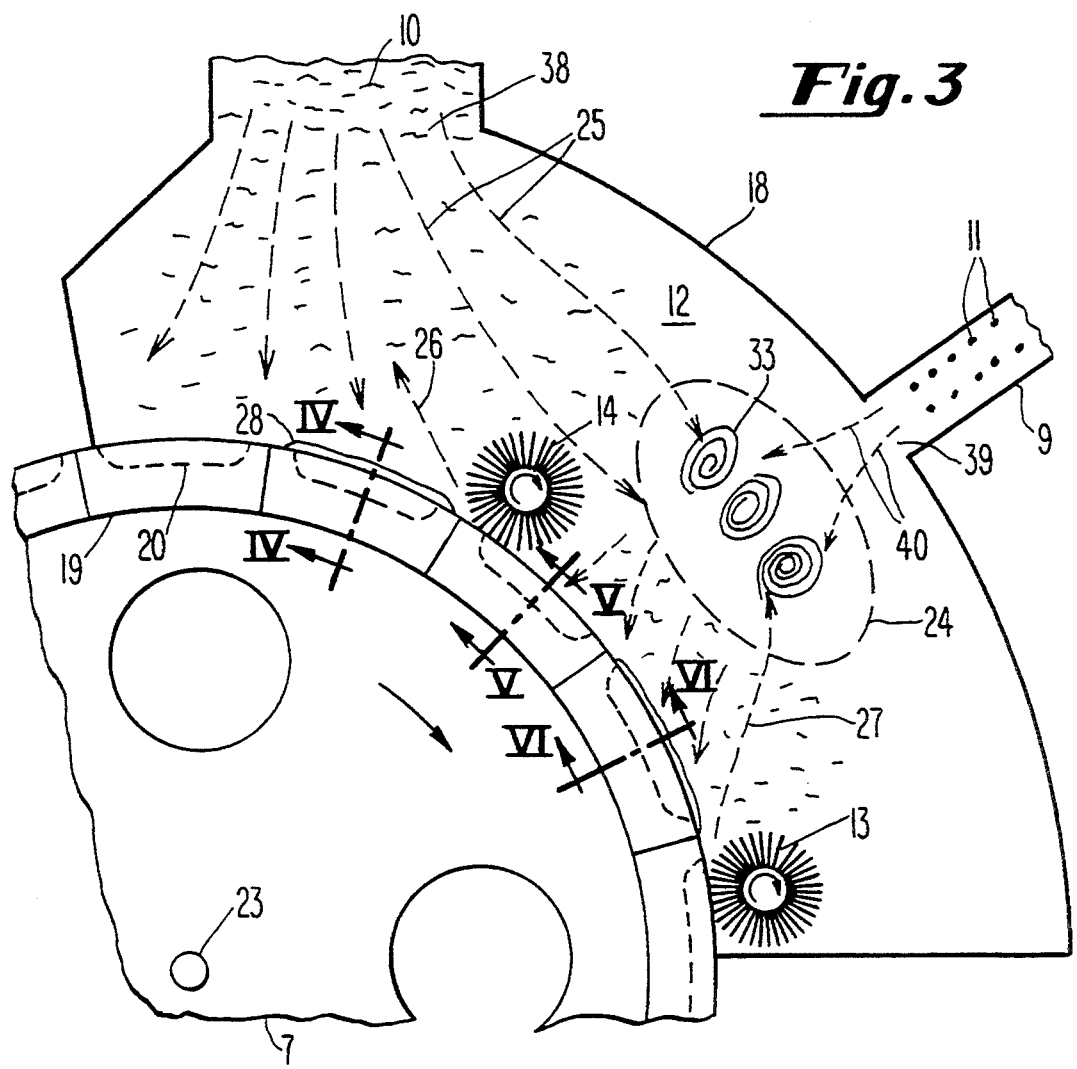
FIG. 3 is a detailed view of the vacuum forming chamber portion of the apparatus shown in FIG. 1.

The superabsorbent particles 11 are directed by the inlet 39 into the vacuum forming chamber 12 in streams 40, shown in FIG. 3. In the preferred embodiment, gravity and suction from the vacuum forming chamber 12 are relied upon to drive the superabsorbent particles 11 into the vacuum forming chamber. However, the hopper 8 could also be pressurized if desired, to impart added velocity to the superabsorbent particle streams 40.

Figure 2:
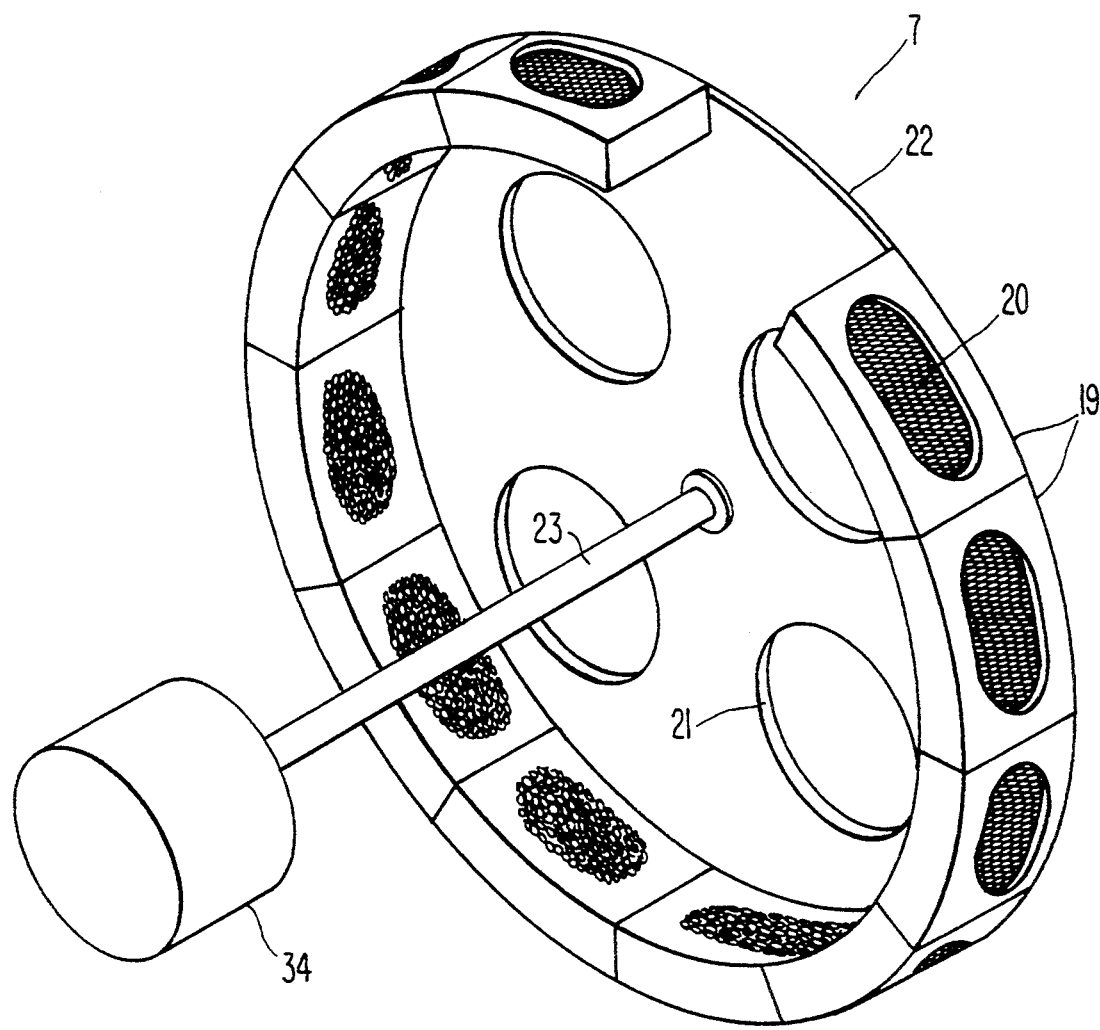
FIG. 2 is an isometric view of the forming wheel of the apparatus shown in FIG. 1.

The forming wheel 7 is mounted for rotation within the housing 18 of the vacuum forming chamber 12 and places the vacuum forming chamber in flow communication with a duct 6 through which air is drawn by the vacuum source 5. As shown in FIG. 2, a number of molds 19 are arranged circumferentially around the periphery of the forming wheel 7. In addition, the forming wheel 7 has a backing plate 22 in which passages 21 are formed that place the duct 6 from the vacuum source 5 in flow communication with the molds 19. A shaft 23 is mounted on the backing plate 22 and is coupled to a motor 34, via a speed reducing device (not shown), that drives the rotation of the forming wheel 7.

As shown in FIG. 3, two scarfing brushes 13 and 14 are disposed within the vacuum forming chamber 12 and are located so as to scarf from the molds any fluff 10 that projects above the outward facing surface of the mold 19. As is conventional, the scarfing brushes 13 and 14 rotate in the same direction as the forming wheel 7.

Figure 4:
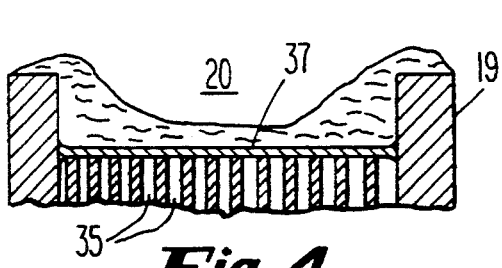
FIGS. 4–6 are cross-sections taken through lines IV—IV, V—V, and VI—VI, respectively, shown in FIG. 3, showing various stages of the product formation as the mold travels through the vacuum forming chamber.
Figure 7:
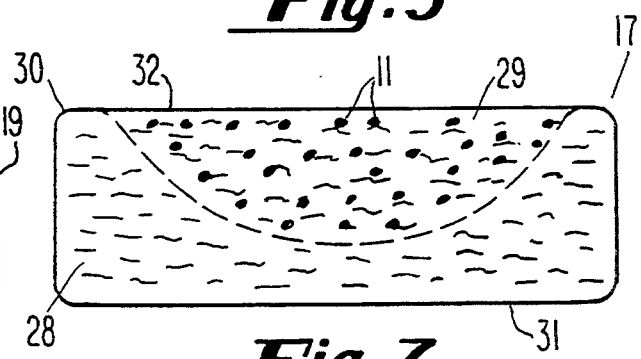
FIG. 7 is a cross-section through the completed absorbent core.

As shown in FIGS. 2 and 4, each of the molds 19 has a cavity 20 that has the shape of the absorbent product to be made by the apparatus, in the preferred embodiment, the absorbent core of an absorbent product such as sanitary napkin, shown in FIG. 7. A screen 37 is disposed in the bottom of the mold cavity 20 and rests atop the outlets of a number of air passages 35 formed within the body of the mold 19. Thus, the vacuum source 5 draws air from the vacuum forming chamber 12 by causing it to flow through the cavity 20, screen 37 and passages 35 of each of the molds 19.

Returning to FIG. 1, a take-off wheel 15 removes the absorbent products 17 from the molds 19, after they have exited from the vacuum forming chamber 12, and deposits them onto a conveyor 16 for further processing. In the case of a sanitary napkin, such further processing would include the application of a fluid permeable cover and a fluid impervious barrier to the body facing side 31 and garment facing side 32, respectively, shown in FIG. 7, of the product.

With reference to FIG. 3, the operation of the apparatus 1 will now be explained in detail. As each mold 19 enters the vacuum forming chamber 12 and begins its passage through it, as a result of the rotation of the forming wheel 7, air is drawn through the molds by the vacuum source 5. As they enter the vacuum forming chamber 12, the molds are first placed into proximity with the fluff inlet 38. As a result, fluff 10 from the incoming streams 25 is gradually deposited within the mold cavities 20 and onto the mold surfaces. As shown in FIG. 4, this results in a mold cavity 20 that is partially filled with a bottom layer of pure fluff 10.

Figure 5:
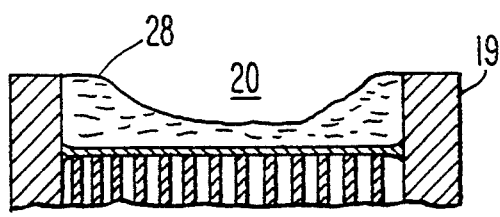

Further rotation of the forming wheel 7 brings the molds 19 into contact with the first scarfing brush 14, which scarfs excess fluff 10 that projects above the surface of the mold and directs it in a stream 26 into the incoming streams 25 of fluff. As a result, a mold 19 that is clean shaven but still only partially filled with a layer 28 of pure fluff 10, as shown in FIG. 5, exits from the scarfing brush 14.

For reasons that will become apparent, it is important that the forming wheel 7 rotate with sufficient speed so that the cavity 20 is only partially filled by the time the mold exits the scarfing brush 14 and begins being filled with a mixture of fluff and superabsorbent particles from a mixing zone 24, as discussed further below. In the preferred embodiment, the forming wheel is rotated with sufficient speed that the cavity 20 is only about half filled by the layer 28 of pure fluff 10 before the deposition of the fluff/superabsorbent particle mixture begins.

Continued rotation of the forming wheel 7 brings the molds into proximity with the superabsorbent particle inlet 39 and, more significantly, with a mixing zone 24 in which superabsorbent particles 11 and fluff 10 are mixed. According to an important aspect of the current invention, the fluff inlet 38 and the superabsorbent particle inlet 39 are spaced around the periphery of the vacuum forming chamber housing 18 so that a portion of the incoming streams 25 of fluff 10 and a portion of the incoming streams 40 of superabsorbent particles 11 collide in a discrete area, referred to as the mixing zone 24, of the vacuum forming chamber 12 just downstream of the scarfing brush 14.

Figure 6:
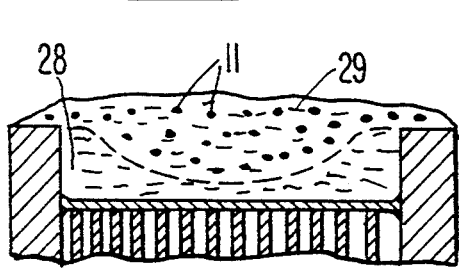

Streams 27 of fluff/superabsorbent particle mixture from the mixing zone 24 are drawn to the partially filled mold cavity 20 so as to completely fill it with a layer 29 of the mixture, as shown in FIG. 6. Next, the mold 19 is rotated under the second scarfing brush 13, which rotates in the same direction as scarfing brush 14 and scarfs any excess fluff/superabsorbent particle mixture that extends above the surface of the mold.

According to an important aspect of the current invention, the scarfing brush 13 is located so that it directs the scarfed fluff/superabsorbent particle mixture in a stream 27 back into the mixing zone 24. In the preferred embodiment, the scarfing brushes 13 and 14 are each about four inches in diameter and are spaced about 20° apart (i.e., about eight inches). By directing the scarfed fluff/superabsorbent particle mixture into the mixing zone 24 turbulence, indicated by reference numeral 33 in FIG. 3, is created within the mixing zone 24 that aids in mixing the superabsorbent particles 11 within the fluff 10. In addition, the continual recycling of the fluff/superabsorbent particle mixture scarfed from the mold 19 back into the mixing zone 24 ensures that virtually complete mixing of the fluff 10 and superabsorbent particle 11 is achieved within the mixing zone. Consequently, the superabsorbent particles 11 are thoroughly dispersed throughout the upper layer 29 of the absorbent product 17, as shown in FIG. 7.

The absorbent product 17 made by the apparatus and process described above, as shown in FIG. 7, enjoys several advantages over products made by traditional approaches in which the superabsorbent particles are confined to a localized layer. Since the superabsorbent particles 11 are well dispersed throughout the product, the gel block to which localized superabsorbent particle layers are subject is much less likely to occur.

Moreover, by filling a portion of the mold cavity 20 with a layer 28 of pure fluff 10, according to the preferred embodiment of the invention, and then orienting the product so that the pure fluff layer 28 forms the body facing side 31 of the napkin, and the mixed fluff-/superabsorbent particle layer 29 forms the garment facing side 32, has an advantage over products in which the superabsorbent particles 11 are dispersed throughout the entire product. Specifically, the pure fluff layer 28 is better equipped than a fluff/superabsorbent particle layer to rapidly accept large quantities of fluid directly from the body and distribute it throughout the product. After accepting the fluid, the pure fluff layer 28 can then distribute it to the fluff/superabsorbent particle layer 29 where the superior absorbing capacity, but slower absorbing rate, of the superabsorbent particles 11 can be effectively utilized.

In the event the invention were practiced utilizing heat activated fibers as the second material 11, rather than superabsorbent particles, the product of the current invention also has advantages over products made using the traditional approach. Although heat activated fibers 11 can perform a valuable function in serving to bind the fluff 10 into a unitized product, they can render the product uncomfortably stiff when confined to a localized layer, as occurs when traditional forming techniques are utilized. However, when the heat activated fibers 11 are thoroughly dispersed throughout at least a portion of the product, they not only bind the fluff fibers 10 more effectively, they do not create as large an increase in stiffness.

Filling a portion of the mold cavity 20 with a layer 28 of pure fluff 10, according to the preferred embodiment of the invention, and then orienting the product so that the pure fluff layer 28 forms the body facing side 31 of the napkin, and the mixed fluff/heat activated fiber layer 29 forms the garment facing side 32, has an advantage over products in which the heat activated fibers 11 are dispersed throughout the entire product. Specifically, the pure fluff layer 28 has the advantage of a soft feel against the user's body.

The present invention may be embodied in other specific forms without departing from the spirit or essential attributes thereof and, accordingly, reference should be made to the appended claims, rather than to the foregoing specification, as indicating the scope of the invention.

What we claim:

1. An apparatus for making absorbent products containing a first material and a second material dispersed throughout at least a portion of said first material, comprising:
   a) a forming chamber having a mixing zone therein for mixing said first and second materials;
   b) first and second means for introducing first and second discrete streams of materials into said forming chamber at first and second locations therein, respectively, said first stream comprising a first material and said second stream comprising a second material;
   c) inducing means for inducing at least a portion of each of said first and second streams of materials introduced into said forming chamber to enter said mixing zone so as to form a mixture thereof and for inducing said mixture to be deposited onto a surface disposed within said forming chamber; and
   d) first removing and directing means for removing from said surface at least a portion of said mixture deposited thereon and for directing said mixture removed into said mixing zone for mixing with said first and second streams of materials.

2. The apparatus for making absorbent products according to claim 1, wherein said inducing means comprises a vacuum source in flow communication with said surface.

3. The apparatus for making absorbent products according to claim 1, wherein said surface comprises a surface of a mold.

4. The apparatus for making absorbent products according to claim 1, wherein said first removing and directing means comprises a scarfing brush.

5. An apparatus for making absorbent products containing a first material and a second material dispersed throughout at least a portion of said first material, comprising:
   a) a chamber forming a mixing zone therein for mixing said first and second materials;
   b) means for introducing said first and second materials into said chamber comprising spaced apart first and second inlet ports, said mixing zone being formed between said first and second inlet ports;
   c) inducing means for inducing at least a portion of said first and second materials introduced into said chamber to be deposited onto a surface disposed within said chamber; and
   d) first removing and directing means for removing from said surface at least a portion of said first and second materials deposited thereon and for directing said materials removed into said mixing zone for mixing of said first and second materials.

6. The apparatus for making absorbent products according to claim 5, wherein said surface comprises a surface of a mold, and further comprising means for transporting said mold sequentially past said first inlet port, then past said mixing zone, and then past said first removing and directing means.

7. The apparatus for making absorbent products according to claim 6, wherein said mold transporting means comprises a wheel mounted for rotation through said chamber.

8. The apparatus for making absorbent products according to claim 5, wherein said surface comprises a surface of a mold, said mold having a cavity formed therein, and wherein said first inlet port is displaced sufficiently far from said mixing zone so that at least a portion of said first material introduced into said chamber by said first inlet port is deposited into said cavity by said inducing means without passing through said mixing zone.

9. The apparatus for making absorbent products according to claim 8, further comprising second removing means for removing from said surface at least a portion of said first material deposited thereon without passing through said mixing zone.

10. The apparatus for making absorbent products according to claim 9, further comprising means for transporting said mold sequentially past said first inlet port, then past said second removing means, then past said mixing zone, and then past said first removing means.

11. The apparatus for making absorbent products according to claim 1, wherein fluff is disposed within said first means for introducing a discrete stream of material, whereby said first material comprises said fluff.

12. The apparatus for making absorbent products according to claim 11, wherein a superabsorbent is disposed within said second means for introducing a discrete stream of material, whereby said second material comprises said superabsorbent.

13. The apparatus for making absorbent products according to claim 1, wherein a superabsorbent is disposed within said second means for introducing a discrete stream of material, whereby said second material comprises a superabsorbent.

14. The apparatus for making absorbent products according to claim 1, wherein heat activated fibers are disposed within said second means for introducing a discrete stream of material, whereby said second material comprises said heat activated fibers.

15. The apparatus for making absorbent products according to claim 1, wherein baking soda is disposed within said second means for introducing a discrete stream of material, whereby said second material comprises said baking soda.

16. An apparatus for making absorbent products containing a first material and a second material dispersed throughout at least a portion of said first material, comprising:
 a) a forming chamber having a mixing zone therein for mixing said first and second materials;
 b) means for introducing first and second discrete streams of said first and second materials, respectively, into said mixing zone so as to form a mixture of said first and second materials within said chamber;
 c) a mold having a surface formed thereon and a cavity in the shape of said absorbent product;
 d) means for transporting said mold through said forming chamber;
 e) a vacuum source for drawing at least a portion of said mixture formed in said mixing zone onto said mold surface and into said cavity while said mold is being transported through said forming chamber; and
 f) means for removing from said mold surface at least a portion of said mixture drawn thereon and for recycling said mixture removed into said mixing zone for further mixing of said first and second materials.

17. An apparatus for making absorbent products containing first and second materials, said first material being an absorbent fluff, comprising:
 a) a chamber having a first inlet for receiving absorbent fluff and a second inlet for receiving a second material;
 b) a plurality of molds, each having a cavity formed in a surface thereof, each of said cavities being substantially in the shape of said absorbent product and in flow communication with a vacuum source;
 c) a material removing device for removing material from said surfaces of said molds and for directing said material removed away from said surfaces; and
 d) a transporting device for transporting said molds through said chamber so as to place said chamber in flow communication with said vacuum source and so as to place said molds sequentially (i) into proximity with said first inlet, whereby absorbent fluff from said first inlet is deposited onto said mold, (ii) then into proximity with said second inlet, whereby a mixture of absorbent fluff and said second material is deposited onto said mold, and (iii) then into proximity with said material removing device, whereby a portion of said mixture of absorbent fluff and second material deposited onto said mold is removed therefrom and directed away from said mold surface.

18. The apparatus for making absorbent products according to claim 17, wherein said second inlet is adapted to direct said second material into said chamber in a stream.

19. The apparatus for making absorbent products according to claim 18, wherein said removing device is located so as to direct at least a portion of said mixture of absorbent fluff and second material removed from said mold surface into mixing contact with said second material stream.

20. The apparatus for making absorbent products according to claim 17, wherein said first inlet has means for directing said absorbent fluff into said chamber in a stream and is located so as to direct at least a portion of said absorbent fluff stream into mixing contact with said second material received by said second inlet.

21. The apparatus for making absorbent products according to claim 17, wherein said material removing device is a scarfing brush.

22. The apparatus for making absorbent products according to claim 17, wherein said material removing device is a first material removing device, and further comprising a second material removing device for removing material from said surfaces of said molds, said transporting device adapted to transport each of said molds into proximity with said second material removing device after transporting said mold into proximity with said first inlet but before transporting said mold into proximity with said second inlet, whereby said second material removing device removes at least a portion of said absorbent fluff from said first inlet that is deposited onto said mold surface.

23. The apparatus for making absorbent products according to claim 17, wherein:
 a) each of said mold cavities includes first and second portions;
 b) said transporting device has a driver for driving said transporting device with sufficient speed so that only said first portion of each of said mold cavities is filled by said deposited absorbent fluff from said first inlet prior to said molds being transported into proximity with said second inlet; and
 c) said driver is capable of driving said transporting device with sufficient speed so that said second portion of each of said mold cavities is filled by said deposited mixture of absorbent fluff and second material prior to said molds being transported into proximity with said material removing device.

24. The apparatus for making absorbent products according to claim 17, wherein said transporting device comprises a wheel, said molds disposed around the periphery of said wheel.

25. The apparatus for making absorbent products according to claim 17, further comprising particles of a superabsorbent material disposed in said second inlet, whereby said particles of superabsorbent form said second material.

26. A method for making absorbent products containing a first material and a second material dispersed throughout at least a portion of said first material, comprising the steps of:
   a) introducing first and second discrete streams of first and second materials, respectively, into a forming chamber and drawing said streams therethrough so that at least first portions of each of said first and second discrete streams meet in a mixing zone, thereby forming a mixture of said first and second materials in which said second material is dispersed throughout said first material;
   b) transporting a forming surface having a cavity therein through said forming chamber;
   c) drawing said mixture from said mixing zone and depositing said mixture onto said forming surface and into a first portion of said cavity while said forming surface is being transported through said cavity;
   d) drawing a substantially pure second portion of said first stream and depositing said second portion onto said forming surface and into a second portion of said cavity while said forming surface is being transported through said cavity; and
   e) removing at least a portion of said mixture deposited onto said forming surface and directing said portion removed into said mixing zone, thereby creating turbulence within said mixing zone, whereby said second material is further dispersed throughout said first material.

27. The method according to claim 26, wherein said forming surface comprises a surface of a forming wheel in which a plurality of mold cavities are disposed for forming said absorbent product.

28. A method for making absorbent products containing a first material and a second material dispersed throughout at least a portion of said first material, comprising the steps of:
   a) introducing first and second streams of first and second materials, respectively, into a chamber;
   b) drawing a substantially pure first portion of said first material stream introduced into said chamber into a cavity of a mold for forming said absorbent product so as to fill a first portion of said mold cavity;
   c) drawing said streams introduced into said chamber through said chamber so that a second portion of said first material stream and at least a portion of said second material stream meet in a mixing zone, thereby forming a mixture of said first and second materials in which said second material is dispersed throughout said first material; and
   d) drawing said mixture from said mixing zone and depositing said mixture onto said mold so that at least a portion of said mixture deposited onto said mold fills a second portion of said mold cavity, the step of depositing said mixture onto said mold so as to fill said second portion of said mold cavity being performed after the step of filling said first portion of said mold cavity with said substantially pure first portion of said first material; and
   e) removing at least a portion of said mixture deposited onto said mold and directing said portion removed into said mixing zone, thereby creating turbulence within said mixing zone, whereby said second material is further dispersed throughout said first material.

29. The method according to claim 28, wherein said first and second portions of said mold cavity form substantially the entirety of said mold cavity.

30. The apparatus for making absorbent products according to claim 1, wherein said first and second locations are spaced apart around said chamber.

31. The method according to claim 28, wherein said first material comprises fluff.

32. The method according to claim 31, wherein said second material comprises a superabsorbent.

33. The method according to claim 28, wherein said second material comprises a superabsorbent.

34. The method according to claim 28, wherein said second material comprises heat activated fibers.

35. The method according to claim 28, wherein said second material comprises baking soda.

* * * * *